United States Patent [19]
Khalil et al.

[11] Patent Number: 5,284,139
[45] Date of Patent: Feb. 8, 1994

[54] HEMOMETRIX TEMPERATURE COMPENSATION

[75] Inventors: Gamal-Eddin Khalil, Bellevue; David P. Brown, Edmonds, both of Wash.

[73] Assignee: Abbot Laboratories, Abbott Park, Ill.

[21] Appl. No.: 815,925

[22] Filed: Dec. 30, 1991

[51] Int. Cl.⁵ .......................... A61B 5/00; A61B 5/02; G01N 33/48; F21V 9/16
[52] U.S. Cl. ..................................... 128/634; 128/632; 128/635; 128/666; 356/41; 250/459.1
[58] Field of Search ........ 128/666, 664, 665, 632-635, 128/637; 356/39-41; 250/458.1, 459.1

[56] References Cited

U.S. PATENT DOCUMENTS

| | | | |
|---|---|---|---|
| 4,016,864 | 4/1977 | Sielaff et al. | 128/632 |
| 4,685,463 | 8/1987 | Williams | 128/632 |
| 4,690,147 | 9/1987 | Ooe et al. | 128/635 |
| 4,697,593 | 10/1987 | Evans et al. | 356/41 X |
| 4,741,343 | 5/1988 | Bowman et al. | 128/635 |
| 4,752,115 | 6/1988 | Murray, Jr. et al. | 356/41 X |
| 4,798,207 | 1/1989 | Wade | 128/632 |
| 4,975,175 | 12/1990 | Karube et al. | 128/635 X |
| 4,994,396 | 2/1991 | Lefkowitz et al. | 356/41 X |
| 5,030,420 | 9/1991 | Bacon et al. | 250/458.1 X |
| 5,043,285 | 8/1991 | Surgi | 250/458.1 X |
| 5,043,286 | 8/1991 | Khalil et al. | 250/459.1 X |
| 5,047,208 | 9/1991 | Schweitzer et al. | 356/39 X |
| 5,047,627 | 9/1991 | Yim et al. | 356/39 X |
| 5,054,487 | 10/1991 | Clarke | 356/39 X |
| 5,058,588 | 10/1991 | Kaestle | 356/41 X |
| 5,090,818 | 2/1992 | Kleineman | 250/458.1 X |
| 5,094,958 | 3/1992 | Klainer et al. | 250/458.1 X |
| 5,102,625 | 4/1992 | Milo | 250/458.1 X |
| 5,115,811 | 5/1992 | Hartlaub et al. | 356/39 X |
| 51,27,407 | 7/1992 | Tan | 356/41 X |
| 5,128,102 | 7/1992 | Kahekoe et al. | 250/459.1 X |
| 5,149,503 | 9/1992 | Kohno et al. | 356/39 X |
| 5,151,603 | 9/1992 | Nakamara | 250/459.1 X |
| 5,173,432 | 12/1992 | Lefkowitz et al. | 128/633 X |
| 5,184,618 | 2/1993 | Wider et al. | 128/634 |
| 5,186,173 | 2/1993 | Zuckerman | 128/633 |
| 5,190,039 | 3/1993 | Takeuchi et al. | 128/633 |

Primary Examiner—Randall L. Green
Assistant Examiner—Elizabeth M. Burke
Attorney, Agent, or Firm—Christensen, O'Connor, Johnson & Kindness

[57] ABSTRACT

A method for converting a value for the partial pressure of oxygen ($pO_2$) in blood at a measurement temperature to a corresponding value at a reference temperature (37° C.). A value for $pO_2$ is determined by measurements made in a patient's blood stream using a phosphorescent compound that is sensitive to the concentration of oxygen. The phosphorescent compound is illuminated with a short pulse of light, causing it to produce a phosphorescent emission having a rate of decay that varies as the function of the partial pressure of oxygen in the blood surrounding the phosphorescent compound. A detector produces an electrical signal corresponding to the intensity of the phosphorescent emission, and the electrical signal is converted to a corresponding digital value for input to a microcomputer. Also supplied to the microcomputer in digital form is a signal indicative of the temperature at the measurement site where the phosphorescent compound is disposed. The microcomputer determines the phosphorescent decay rate and from that value, determines the $pO_2$ at the measurement site for the temperature at which the measurement was made. An initial estimate of a corresponding value for $pO_2$ at the reference temperature is made as a function of the measurement temperature and the $pO_2$ at that temperature. A more accurate estimate of $pO_2$ at the reference temperature is iteratively determined by successively evaluating an expression that is a function of the initial measurement and a previous more accurate estimate. If the measurement temperature is less than the reference temperature, the current more accurate estimate is replaced by the average of the previous two estimates. A final more accurate estimate representing the value for $pO_2$ at the reference temperature is then displayed.

20 Claims, 4 Drawing Sheets

HEMOMETRIX TEMPERATURE COMPENSATION

FIELD OF THE INVENTION

The present invention generally relates to a method for determining a partial pressure of oxygen in blood, and more specifically, to a method for determining a partial pressure of oxygen at a reference temperature, as a function of a partial pressure of oxygen measured at a different temperature.

BACKGROUND OF THE INVENTION

In conventional blood gas analysis machines, a sample of blood withdrawn from a patient is heated to a reference temperature of 37° C. before the partial pressure of oxygen ($pO_2$) is determined. Over time, the medical community has thus developed a preference for reporting all $pO_2$ measurements referenced to 37° C. However, when $pO_2$ is measured in vivo instead of in a blood gas analyzer, the measurement is often made at a substantially different temperature even though 37° C. is normal body temperature. For example, during certain surgical procedures, it is necessary to lower the patient's body temperature by as much as 20° C., thereby depressing metabolic activity. If the $pO_2$ measurement is made while the patient's body is chilled, the result is very different than a corresponding measurement made at 37° C. An anesthesiologist controlling the administration of oxygen and other gases to the patient typically prefers to record the $pO_2$ at the accepted reference temperature of 37° C. rather than the lower measurement. Moreover, the anesthesiologist may prefer to base decisions concerning the patient's condition on $pO_2$ data referenced to 37° C. When making such decisions during a critical operation, the anesthesiologist may not have time to draw a sample of blood for analysis in a blood gas analyzer at the reference temperature. An in vivo, real time determination of $pO_2$ is sometimes essential, even if carried out at a different measurement temperature than the desired 37° C. reference.

Conversion between a $pO_2$ measurement at one temperature to that at another temperature is not a trivial task. The solubility of oxygen in blood as a function of temperature is determined by a non-algebraic combination of transcendental functions. As a result, it is not possible to analytically solve a simple equation to convert a $pO_2$ measurement at a substantially different temperature to a corresponding value at the desired reference temperature of 37° C. In the past, medical personnel have been forced to manually convert a measured value for $pO_2$ to the 37° C. reference temperature using a nomogram or by interpolating values from a look-up table. Neither of these techniques are particularly desirable when speed in determining the data is essential; furthermore, any human errors in the conversion process can have potentially life-threatening consequences.

The complex relationship between temperature and $pO_2$ is evident from the equation that has been developed in the prior art to convert from a $pO_2$ measurement made at 37° C. to a different temperature. This equation is reported by R. A. Ashwood, G. Kost, and M. Kenny in "Temperature Correction of Blood-Gas and pH Measurements," Clinical Chemistry, Vol. 29, 11:1877–1885, 1983 and by J. W. Severinghaus in "Simple, Accurate Equations for Human Blood $O_2$ Dissociation Computations," American Journal of Physiology, Vol. 46, 3:599–602. The equation in both of these references is as follows:

$$pO_{2PT} = pO_{2REF} 10^{(\frac{T-37}{2.303})} \left( \frac{0.058}{.243(\frac{pO_{2REF}}{100})^{3.88}+1} + 0.013 \right) \quad (1)$$

where $pO_{2PT}$ is the predicted partial pressure of oxygen at a temperature T that is different than the reference temperature, and $pO_{2REF}$ is the measured partial pressure of oxygen at the reference temperature (37° C.). One might assume that equation 1 could simply be rearranged to determine $pO_2$ at the reference temperature from the $pO_2$ measured at a temperature different than the reference temperature, i.e., as follows:

$$pO_{2REF} = pO_{2M} 10^{(\frac{T-37}{2.303})} \left( \frac{0.058}{.243(\frac{pO_{2M}}{100})^{3.88}+1} + 0.013 \right) \quad (2)$$

where $pO_{2M}$ is the partial pressure of oxygen measured at the temperature T. However, Equation 2 produces erroneous results due to the nature of the mathematical relationship between measurement temperature and $pO_2$. In the above-noted paper, Severinghaus recognized the difficulty of calculating $pO_2$ at 37° C. based on measurements made at other temperatures. On page 600 of the Journal, he suggests that, "[t]o begin with some other temperature, one may estimate a trial 37° C. $pO_2$ using the factors 6%/°C. if $pO_2 < 100$, and 6 Torr/°C. above 100 Torr, and proceed iteratively in Eq. (3)." (Equation 3 in the reference is equivalent to Equation 1, above.) What Severinghaus intended by this statement is not entirely clear, because he did not present any example of how the iterative process is carried out nor any support for its efficacy in producing an accurate result.

Accordingly, a method is required for quickly determining the $pO_2$ of a patient's blood at the reference temperature, based on a measurement made at another temperature. The method should be automatically carried out to avoid human error and must be implemented quickly (in real time) to make the results of an in vivo measurement of $pO_2$ at the patient's temperature immediately available as a corresponding value at the reference temperature during critical medical procedures.

SUMMARY OF THE INVENTION

In accordance with the present invention, a method for determining a partial pressure of oxygen at a predefined reference temperature during an in vivo blood gas measurement begins with the step of measuring $pO_2$ at an arbitrary temperature (that is substantially different than the reference temperature), as a function of a physical parameter that changes to indicate the $pO_2$ at a measurement site. The measurement includes the steps of producing a first signal indicative of the $pO_2$ in response to changes in the physical parameter; producing a second signal indicative of the arbitrary temperature at the measurement site; and processing the first signal to determine the $pO_2$ at the arbitrary temperature. Next, an estimate of the $pO_2$ at the predefined reference temperature is determined as a function of the first signal and of the second signal. After the initial estimate is determined, a more accurate estimate of $pO_2$ at the predefined reference temperature is made as a function of the first signal, the second signal, and the estimate of the pO2 at the predefined reference temperature. Subsequently, the step of determining the more accurate estimate is iteratively repeated, each iteration using the more accurate estimate of the pO2 from a previous iteration as a value for the estimate. After a predefined number of such iterations have been completed, the resulting more accurate estimate approximates the pO2 at the predefined reference temperature corresponding to the measurement of the pO2 made at the arbitrary temperature.

Each iteration determines the more accurate estimate, as defined by the equation:

$$X_{N+1} = X_0 10^{(\frac{T_R - T}{K_1})(f(X_N))}$$

where $X_0$ is the pO2 measured at the arbitrary temperature; T is the arbitrary temperature; $T_R$ is the predefined reference temperature; $X_{N+1}$ is the more accurate estimate of the pO2 for an (N+1)th iteration; $X_N$ is the more accurate estimate of the pO2 for the Nth iteration; $K_1$ is a predetermined constant; and $f(X_N)$ is a predefined function of $X_N$. The function $f(X_N)$ is represented by:

$$f(X_N) = \frac{K_2}{K_3 \left(\frac{X_N}{K_4}\right)^{K_4} + K_5} + K_6$$

where $K_2$ through $K_6$ are predefined constants.

If the arbitrary temperature is less than the reference temperature, for each iteration after the first computed iteration, an average of the previous two estimates of the pO2 at the predefined reference temperature is determined and is used as the value for the estimate in the current iteration to determine the next more accurate estimate. The predefined number of iterations is selected so that the more accurate estimate of the pO2 at the predefined reference temperature converges to a value within a predefined convergence limit. Preferably, the predefined number of iterations is less than ten.

The foregoing aspects and many of the attendant advantages of this invention will become more readily appreciated by reference to the following detailed description, when taken in conjunction with the accompanying drawings.

DETAILED DESCRIPTION OF THE PREFERRED EMBODIMENT

Figure 1:
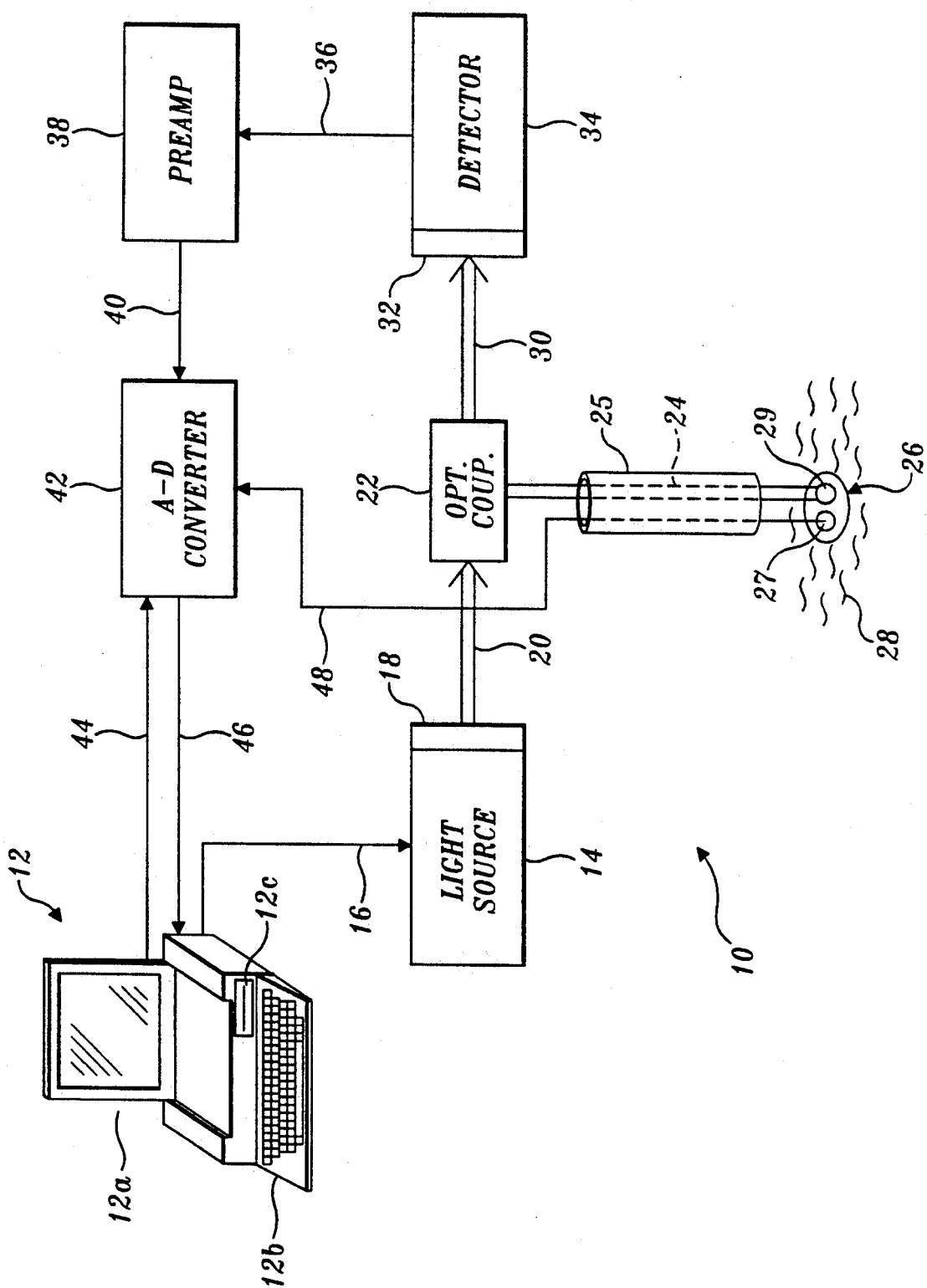
FIG. 1 is a block diagram of a representative system for measuring pO2 at an in vivo measurement site.

A system for monitoring the concentration of oxygen (O2) in blood is shown graphically in a block diagram generally reference 10 in FIG. 1. As is conventional in the medical art, the concentration of O2 in blood is measured in terms of the partial pressure of O2 (pO2). System 10 converts between a measurement of pO2 at a temperature different than a desired reference temperature, which is normally 37° C., the temperature corresponding to normal human body temperature. System 10 determines pO2 at the reference temperature in real time, for example, during an operation so that an anesthesiologist can adjust the relative proportion of oxygen to other gases being administered to the patient, and converts any measurement made at a temperature different than the reference temperature to a corresponding value at the reference temperature. This information is provided to medical personnel so they can make appropriate decisions concerning the patient. As noted above, it is important during such procedures that the conversion from pO2 at a measurement temperature to the corresponding pO2 at the reference temperature be carried out in real time, since medical decisions concerning patient's safety should not be delayed for determination of pO2 in a blood gas analyzer. In certain medical procedures, the patient may be chilled to a temperature as much as 20° C. below normal body temperature, or due to physiological changes affecting the patient's body temperature at which the temperature which the pO2 measurement is made may be substantially higher than the desired reference temperature of 37° C. Accordingly, system 10 automatically displays pO2 at the reference temperature, regardless of the actual temperature at which the pO2 is measured in the patient's blood.

System 10 includes a microcomputer 12, which preferably comprises a laptop or other portable computer having a display 12a, a keyboard 12b, and a floppy disk or hard drive 12c for storing data and programs. Microcomputer 12 controls a light source 14 via a signal supplied to the source over a lead 16, the signal causing light source 14 to emit a short pulse of light at a time $t_0$. The light pulse produced by light source 14 passes through a filter 18 that allows only shorter wave length light, e.g., light having a wave length in the range of 480 to 600 nanometers (nm), to pass through into an optical fiber 20. Optical fiber 20 conveys the filtered light pulse to an optical coupler 22. Optical coupler 22 couples the filtered light pulse into an optical fiber 24, which conveys the filtered light pulse into the patient's body via an intravascular catheter 25 to a pO2 sensor 26 that is disposed within the patient's blood stream 28. Sensor 26 comprises a temperature sensor 27, (for example, a thermistor, thermocouple, or other temperature sensitive element) and a phosphorescent compound 29. Preferably, the phosphorescent compound comprises a fluorinated derivative of platinum tetra(pentafluorophenyl)-porphyrin, Pt(TFPP), which is excited into phosphorescence by light having a wave length in the range 480 to 600 nm, and the phosphorescent emission thereafter decays with a rate that is a function of the concentration of oxygen to which the phosphorescent compound is exposed. The oxygen in the blood stream in which sensor 26 is disposed quenches the phosphorescent emission of this compound, and the rate at which the phosphorescent emission decays is proportional to the pO2 of the blood. The characteristic decay time of the phosphorescent emission produced by phosphorescent compound 29 is thus a measureable parameter indicative of pO$_2$ in blood stream 28. Details of this method for measuring oxygen concentration (i.e., pO$_2$) are fully disclosed in commonly assigned U.S. Pat. No. 4,810,655, the specification and disclosure of which are specifically incorporated herein by reference.

Optical fiber 24 conveys the phosphorescent emission from phosphorescent compound 29 as a return light signal in optical fiber 24 back toward optical coupler 22, wherein it is coupled into an optical fiber 30. Optical fiber 30 conveys the phosphorescent emission from sensor 26 through a cut-off filter 32 that allows only light having a wave length longer than 620 nm to enter an adjacent detector 34. Optical filter 18 and cut-off filter 32 are thus selected to transmit complimentary wave lengths, thereby preventing light from light source 18 from directly reaching detector 34, but enabling the phosphorescent emission to be detected by it.

Detector 34 preferably comprises a photodiode that produces an electrical signal corresponding to the intensity of the phosphorescent emission returning from sensor 26, which is conveyed over leads 36 to a preamplifier 38. Preamplifier 38 amplifies the electrical signal and supplies the amplified signal through leads 40 to an analog-to-digital (A-D) converter 42. A-D converter 42 converts the amplified signal from preamplifier 38 into a corresponding digital signal that is conveyed through leads 46 into an input port (not separately shown) of microcomputer 12. The A-D converter is controlled by a signal output from microcomputer 12 over lines 44 to select either the amplified signal or the analog temperature signal, which is produced by temperature sensor 27, for A-D conversion. This analog temperature signal is indicative of the temperature of blood stream 28, i.e., the temperature at the measurement site, and is conveyed over a lead 48 to A-D converter 42 from temperature sensor 27.

The intensity of the phosphorescent emission is determined by microcomputer 12 at two times, t$_2$ and t$_2$, after the light pulse from light source 14 has terminated. Using these two intensities, the microcomputer determines the simple exponential decay rate of the emission produced by phosphorescent compound 29. Based upon the decay rate, a value for pO$_2$ at the temperature at the measurement site is determined at the temperature sensed by temperature sensor 27. If the temperature at the measurement site is different than the reference temperature of 37° C., microcomputer 12 executes a program to convert the value for pO$_2$ at the measurement temperature into a corresponding value at the reference temperature as described below.

Figure 2:
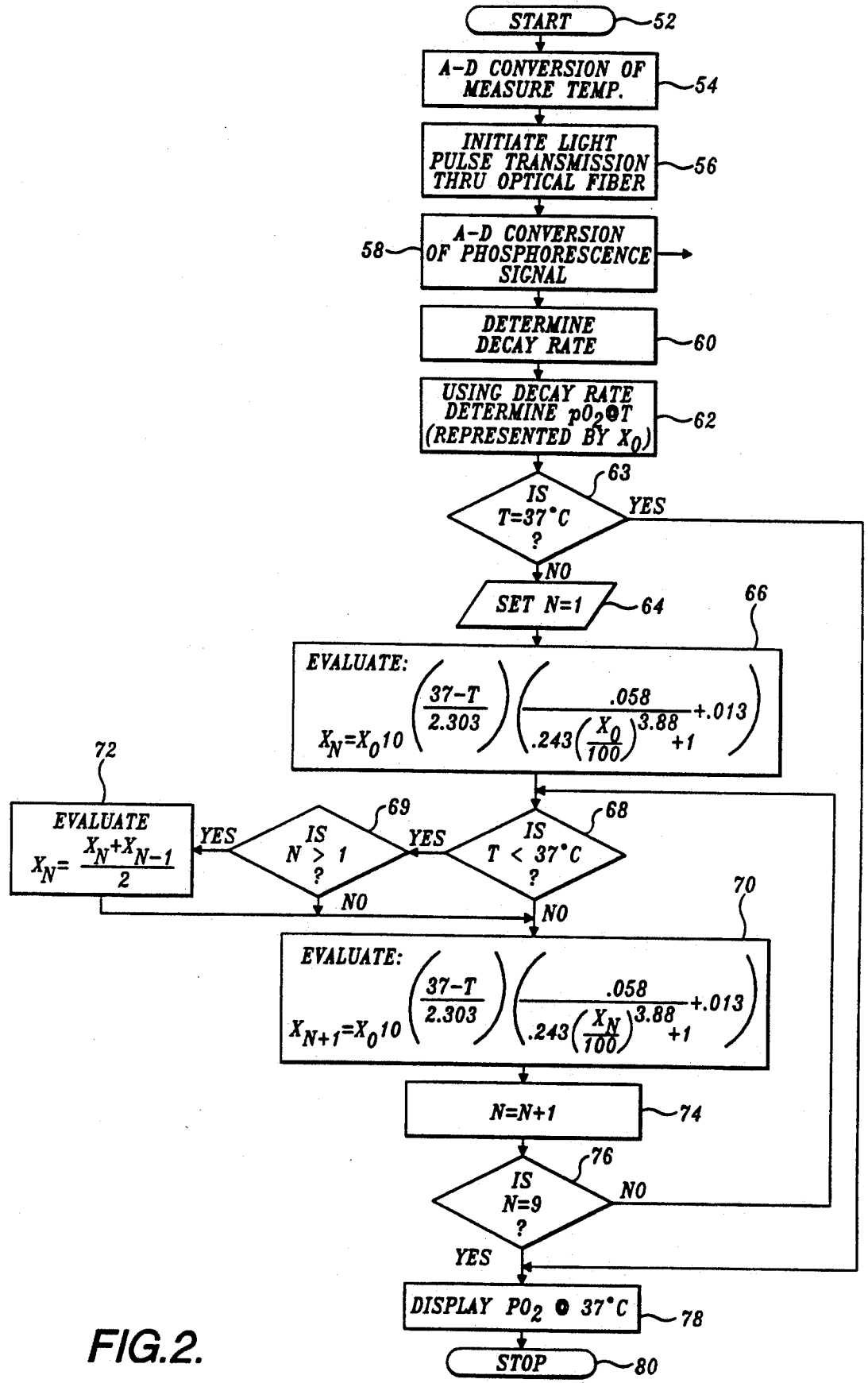
FIG. 2 is a flow chart showing the logical steps required in carrying out the present invention on a central processing unit (CPU)

The logical steps implemented by microcomputer 12 in determining a value for pO$_2$ at the reference temperature based on a measured value at a different temperature are shown in a flow chart 50 (FIG. 2). After a start block 52, a block 54 provides for the analog to digital conversion of the temperature, T, at the measurement site. In a block 56, microcomputer 12 produces a signal causing light source 14 to produce the light pulse, to irradiate phosphorescent compound 29 with light for a short period of time. A block 58 provides for the A-D conversion of the phosphorescence emission produced by phosphorescent compound 29 at times t$_1$ and t$_2$. In a block 60, the decay rate of the phosphorescent emission is determined based upon the exponential relationship of the intensity of light at times t$_1$ and t$_2$. Using the decay rate from block 60, a partial pressure of oxygen, X$_0$, at the measurement temperature T is determined in a block 62. A decision block 63 then determines if T = 37° C., and if so, branches to a block 78 to display the pO$_2$ value to a user on display 12a (shown in FIG. 1). If T is not equal to 37° C., the flow chart continues with a block 64.

Block 64 initializes a counter N to 1. In a block 66, an expression is evaluated to determine a first estimate, X$_N$, for the pO$_2$ at the reference temperature, 37° C., as a function of the measured value for pO$_2$, X$_0$, and as a function of the temperature at the measurement site, T.

$$X_N = X_0 10^{(\frac{37-T}{2.303})} \left( \frac{0.058}{0.243(\frac{X_0}{100})^{3.88} + 1} + 0.013 \right) \quad (3)$$

If the measurement temperature is less than 37° C., a decision block 68 proceeds to a decision block 69. Decision block 69 determines whether N is greater than 1, and if not, the flow chart proceeds to a block 70. However, for subsequent iterations through decision block 68 that occur as described below, an affirmative response to decision block 69 leads to a block 72, wherein an average of the previous two estimates of the pO$_2$ at the reference temperature, 37° C., is determined.

$$X_N = \frac{X_N + X_{N-1}}{2} \quad (4)$$

This average replaces the current estimate, X$_N$, which is used for the next evaluation in block 70. In block 70, a more accurate estimate, X$_{N+1}$, of the pO$_2$ at the reference temperature is determined as a function of the measured pO$_2$, the temperature at the measurement site, and the last estimate X$_N$ of the pO$_2$ at the reference temperature (or its current value based on the average from block 72, for measurements made at a temperature less than the reference temperature).

$$X_{N+1} = X_0 10^{(\frac{37-T}{2.303})} \left( \frac{0.058}{0.243(\frac{X_N}{100})^{3.88} + 1} + 0.013 \right) \quad (5)$$

The flow chart then proceeds to a block 74 wherein N is incremented by one. A decision block 76 determines whether N exceeds a predetermined value representing the number of iterations desired. In the preferred embodiment, this predefined value is 9. If fewer than nine iterations have been made, decision block 76 loops back to decision block 68, iteratively repeating the evaluation to determine the more accurate estimate X$_N$ of the pO$_2$ at the reference temperature. Once the number of iterations has reached the predefined number, block 78 displays the last more accurate estimate of the pO$_2$ at 37° C. for use by medical personnel. Subsequently, the algorithm stops in a block 80 until the value for pO$_2$ at the measurement temperature is updated, which may occur as many as 100 times per second.

Figure 3:
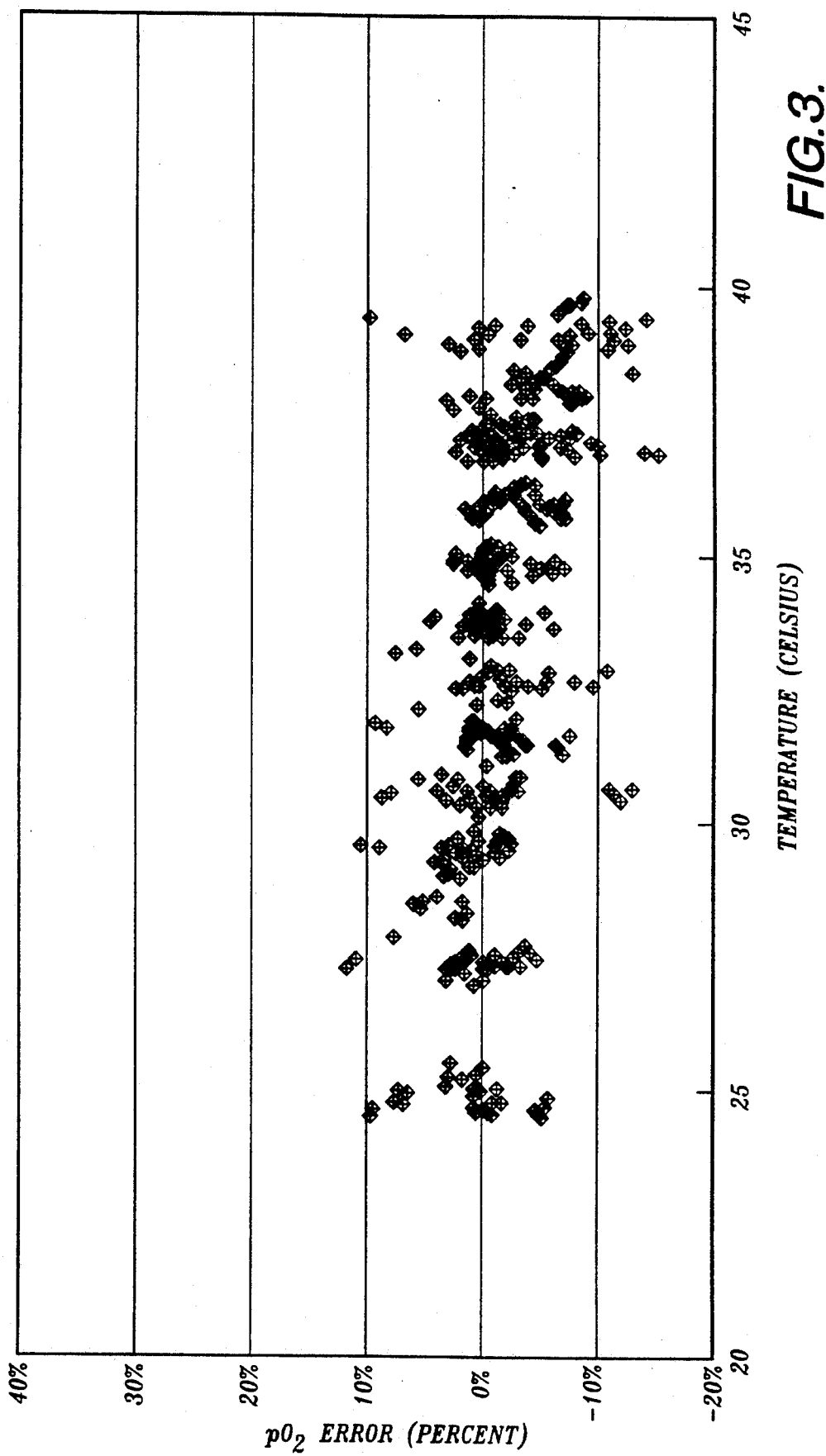
FIG. 3 is a graph showing the per cent error for the determination of pO2 at a number of different measurement temperatures, when the present method is applied to determine a corresponding pO2 at a reference temperature (37° C.)

Referring now to FIG. 3, the result of applying the iterative process to determine the pO$_2$ at the reference temperature is shown in terms of a percentage error for four different pO$_2$ levels and twelve measurement temperatures ranging from approximately 25° C. to 40° C. The percentage errors shown are referenced to measurements of pO$_2$ in blood samples at the reference temperature that were made on a Corning Model 178 blood gas analyzer.

Although a $pO_2$ at the reference temperature can be determined from a measurement at a temperature less than the reference temperature without the averaging step carried out in block 72 of FIG. 2, a greater number of iterations are required to achieve the same acceptable convergence limit. In the preferred embodiment, an acceptable convergence limit is ±0.5 Torr. A maximum of nine iterations are required to achieve this convergence limit, as reflected in decision block 76.

Figure 4:
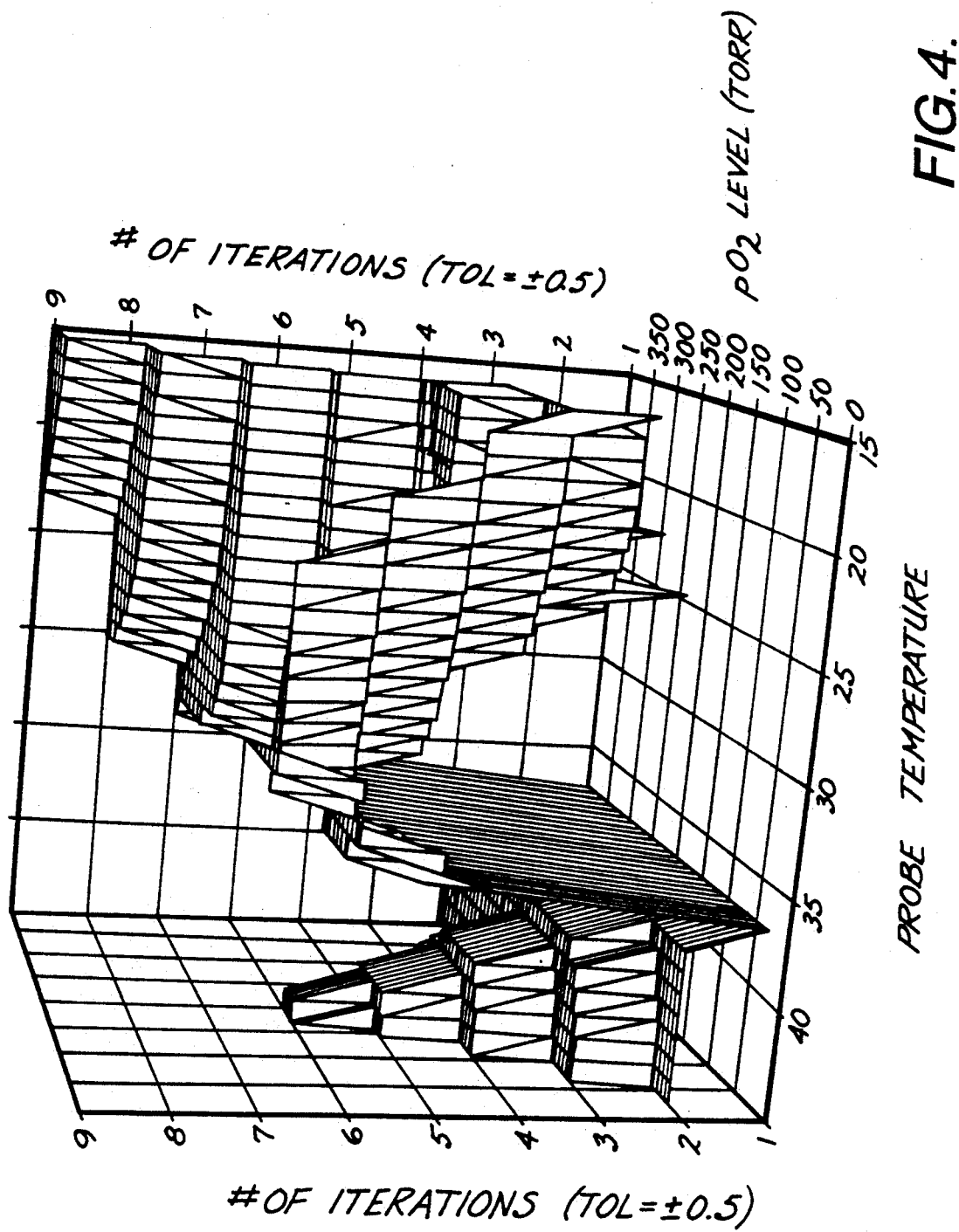
FIG. 4 is a three-dimensional graph showing the relationship between the number of iterations, probe (measurement) temperature, and pO2 level with respect to the present invention.

In FIG. 4, the relationship between measurement temperature, $pO_2$ level, and the number of iterations required to achieve ±0.5 Torr convergence limit are shown in a three-dimensional graph. As shown in this FIGURE, it is only when the measurement temperature is below 25° C. that up to nine iterations are required to achieve the desired accuracy.

Although the method for converting a value for $pO_2$ measured at one temperature to a corresponding value at the reference temperature has been disclosed with respect to measurements made in a patient's blood stream, it should be apparent that the same technique can be applied to other environments, for example, when the measurement is made in a specimen or sample of blood taken from a patient. Furthermore, the method for converting from $pO_2$ at an arbitrary temperature to a corresponding value for the $pO_2$ at the reference temperature of 37° C. is also applicable to other techniques for measuring $pO_2$. While the preferred embodiment of the invention has been illustrated and described, it will be appreciated that various changes can be made therein without departing from the spirit and scope of the invention. Accordingly, it is not intended that the scope of the invention in any way be limited by the disclosure, but instead that it be determined entirely by reference to the claims that follow.

The embodiments of the invention in which an exclusive property or privilege is claimed are defined as follows:

1. A method for determining a partial pressure of oxygen of blood at a predefined reference temperature of blood during an in vivo blood gas measurement, comprising the steps of:
   (a) measuring in vivo a partial pressure of oxygen of blood at an arbitrary temperature that is substantially different than the reference temperature of blood, as a function of a physical parameter that changes to indicate the partial pressure of oxygen of blood at a measurement site, said step of measuring including the steps of:
       (i) producing a first signal indicative of the partial pressure of oxygen of blood, in response to changes in the physical parameter;
       (ii) producing a second signal indicative of the arbitrary temperature of blood at the measurement site; and
       (iii) processing the first signal to determine the partial pressure of oxygen of blood at the arbitrary temperature;
   (b) determining an estimate of a partial pressure of oxygen of blood at the predefined reference temperature of blood as a function of the partial pressure of oxygen of blood at the arbitrary temperature of blood, and of the second signal;
   (c) determining a more accurate estimate of the partial pressure of oxygen of blood at the predefined reference temperature as a function of:
       (i) the partial pressure of oxygen of blood at the arbitrary temperature of blood;
       (ii) the second signal; and
       (iii) the estimate of the partial pressure of oxygen of blood at the predefined reference temperature; and
   (d) iteratively repeating step (c), each iteration using said more accurate estimate of the partial of oxygen of blood from a previous iteration as a value for said estimate in (c)(iii), until a predefined number of such iterations have been completed, a more accurate estimate that results from a last of such iterations approximating the partial pressure of oxygen of blood at the predefined reference temperature corresponding to the measurement of the partial pressure of oxygen of blood made at the arbitrary temperature of blood.

2. The method of claim 1, wherein each iteration of step (c) determines said more accurate estimate as defined by:

$$X_{N+1} = X_0 10^{(\frac{T_R - T}{K_1}) (f(X_N))}$$

where:
$X_0$ is the partial pressure of oxygen of blood measured at the arbitrary temperature of blood;
T is the arbitrary temperature of blood;
$T_R$ is the predefined reference temperature of blood;
$X_{N+1}$ is the more accurate estimate of the partial pressure of oxygen of blood for an (N+1)th iteration;
$X_N$ is the more accurate estimate of the partial pressure of oxygen of blood for an Nth iteration;
$K_1$ is a predetermined constant; and
$f(X_N)$ is a predefined function of $X_N$.

3. The method of claim 2, wherein the predefined function $f(X_N)$ is represented by:

$$f(X_N) = \frac{K_2}{K_3 \left(\frac{X_N}{K_4}\right)^{K_4} + K_5} + K_6$$

where:
$K_2$ through $K_6$ are predefined constants.

4. The method of claim 1, wherein if the arbitrary temperature is less than the reference temperature of blood, the method further comprises the steps of:
   (a) for each iteration after a first iteration, determining an average of the previous two more accurate estimates of the partial pressure of oxygen of blood; and
   (b) using the average as the value for said estimate in a next iteration, in step (c)(iii).

5. The method of claim 1, wherein the predefined number of iterations is selected so that the more accurate estimate of the partial pressure of oxygen of blood at the predefined reference temperature of blood converges to a value within a predefined convergence limit.

6. The method of claim 1, wherein the predefined number of iterations is less than ten.

7. A method for determining a partial pressure of oxygen in a patient's blood, at a predefined reference temperature, comprising the steps of:
   (a) transmitting a light signal to a measurement site in the patient's body, said light signal causing a material sensitive to the light signal to emit a return light signal having a parameter that varies as a function of the partial pressure of oxygen that is present in the blood at the measurement site;

(b) detecting the return light signal, producing an electrical signal corresponding thereto, said electrical signal being indicative of the partial pressure of oxygen at a temperature of the blood at the measurement site;

(c) producing a temperature signal indicative of the temperature of the blood at the measurement site at the time the return light signal is produced, said temperature being substantially different that the reference temperature;

(d) digitizing the temperature signal and the electrical signal;

(e) determining an estimate of a partial pressure of oxygen at the predefined reference temperature as a function of the digitized electrical signal, which represents the partial pressure of oxygen at the temperature of blood at the measurement site, and as a function of the digitized temperature at the measurement site;

(f) determining a more accurate estimate of the partial pressure of oxygen at the predefined reference temperature as a function of:
  (i) the digitized electrical signal;
  (ii) the digitized temperature at the measurement site; and
  (iii) the estimate of the partial pressure of oxygen at the predefined reference temperature; and (g) iteratively repeating step (f), each iteration using said more accurate estimate of the partial pressure of oxygen from a previous iteration as a value for said estimate in (f)(iii), until a predefined number of such iterations have been completed, a more accurate estimate that results from a last of such iterations approximating the partial pressure of oxygen at the predefined reference temperature corresponding to the measurement of the partial pressure of oxygen made at the temperature of blood at the measurement site.

8. The method of claim 7, wherein the step of transmitting comprises the step of exciting the material to phosphorescence, causing it to emit the return light signal as phosphorescent light for a period of time dependent upon the partial pressure of oxygen at the measurement site.

9. The method of claim 7, wherein each iteration of step (f) determines said more accurate estimate as defined by:

$$X_{N+1} = X_0 10^{(\frac{T_R - T}{K_1})(f(X_N))}$$

where:
$X_0$ is the partial pressure of oxygen measured at the temperature of the measurement site;
$T$ is the temperature of the measurement site;
$T_R$ is the predefined reference temperature;
$X_{N+1}$ is the more accurate estimate of the partial pressure of oxygen for an $(N+1)$th iteration;
$X_N$ is the more accurate estimate of the partial pressure of oxygen for an Nth iteration;
$K_1$ is a predetermined constant; and
$f(X_N)$ is a predefined function of $X_N$.

10. The method of claim 9, wherein the predefined function $f(X_N)$ is represented by:

$$X_{N+1} = X_0 10^{(\frac{T_R - T}{K_1})(f(X_N))}$$

where:
$K_2$ through $K_6$ are predefined constants.

11. The method of claim 9, wherein the predefined function $f(X_N)$ is represented by:

$$X_{N+1} = X_0 10^{(\frac{37-T}{2.303})}\left(\frac{.058}{.243(\frac{X_N}{100})^{3.88}+1} + .013\right)$$

12. The method of claim 7, wherein if the temperature at the measurement site is less than the reference temperature, the method further includes the steps of:
  (a) for each iteration after a first iteration, determining an average of the previous two more accurate estimates of the partial pressure of oxygen; and
  (b) using the average as the value for said estimate in a next iteration, in step (f)(iii).

13. The method of claim 7, wherein the predefined number of iterations is selected so that the more accurate estimate of the partial pressure of oxygen at the reference temperature converges to a value within a predefined convergence limit.

14. The method of claim 7, wherein the predefined number of iterations is less than ten.

15. A method for determining a partial pressure of oxygen at a predefined reference temperature at a measurement site disposed on a distal end of an optical fiber within a patient's cardiovascular system, a temperature at said measurement site being substantially different than the reference temperature, comprising the steps of:

(a) conveying a pulse of light through the optical fiber toward its distal end, said light exciting a phosphorescent material disposed on the distal end of the optical fiber into phosphorescence that is quenched at a rate dependent upon the partial pressure of oxygen at the measurement site, producing a return light signal that travels through the optical fiber;

(b) determining a decay time for the return light signal, and based upon the decay time, the partial pressure of oxygen at the measurement site at the temperature of the measurement site;

(c) sensing the temperature of the measurement site, producing a temperature signal indicative of said temperature;

(d) determining a first estimate of the partial pressure of oxygen at the predefined reference temperature as a function of the partial pressure of oxygen that was determined from the decay time and as a function of the temperature signal;

(e) determining a more accurate estimate of the partial pressure of oxygen at the predefined reference temperature as a function of:
  (i) the partial pressure of oxygen that was determined from the decay time;
  (ii) the temperature signal; and
  (iii) the first estimate of the partial pressure of oxygen at the predefined reference temperature; and (f) iteratively repeating step (e), a first such iteration substituting the more accurate estimate of the partial pressure of oxygen at the predefined reference temperature for the first estimate of step (e)(iii), and a subsequent iteration substituting the more accurate estimate of the partial pressure of oxygen determined from the previous iteration for the value previously used in step (e)(iii) in the iteration before, the more accurate estimate from the last of a predefined number of such iterations closely approximating the partial pressure of oxygen at the predefined reference temperature.

16. The method of claim 15, wherein if the temperature at the measurement site is less than the reference temperature, after the first iteration, an average of the previous two more accurate estimates of the partial pressure of oxygen at the reference temperature is substituted for the last estimate in each further iteration.

17. The method of claim 15, wherein the more accurate estimate is defined by:

$$X_{N+1} = X_0 10^{\left(\frac{37-T}{2.303}\right)\left(\frac{.058}{.243\left(\frac{X_N}{100}\right)^{3.88}+1}+.013\right)}$$

where:

$X_0$ is the partial pressure of oxygen determined as a function of the partial pressure of oxygen at the temperature of the measurement site;

T is the temperature of the measurement site;

$X_{N+1}$ is the more accurate estimate of the partial pressure of oxygen for an (N+1)th iteration;

the reference temperature equals 37° C.; and $X_N$ is the more accurate estimate of the partial pressure of oxygen for an Nth iteration.

18. The method of claim 15, wherein the predefined number of iterations is selected to determine a final approximation of the partial pressure of oxygen at the reference temperature that is within an accepted convergence limit.

19. The method of claim 18, wherein the predefined number of iterations is less than ten and the accepted convergence limit is less than ±0.5 Torr.

20. The method of claim 18, wherein fewer iterations are used to obtain a final approximation of the partial pressure of oxygen at the reference temperature that is within the accepted convergence limit when the temperature at the measurement site is greater than the reference temperature, as compared to when it is less.

* * * * *